United States Patent
McCord (10) Patent No.: US 7,465,922 B1
(45) Date of Patent: Dec. 16, 2008

(54) ACCELERATING ELECTROSTATIC LENS GUN FOR HIGH-SPEED ELECTRON BEAM INSPECTION

(75) Inventor: Mark A. McCord, Los Gatos, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 217 days.

(21) Appl. No.: 11/485,542

(22) Filed: Jul. 12, 2006

(51) Int. Cl.
*G01N 23/00* (2006.01)
*G21K 7/00* (2006.01)
*A61N 5/00* (2006.01)
*G21G 5/00* (2006.01)
*G21K 1/08* (2006.01)
*H01J 3/14* (2006.01)
*H01J 3/26* (2006.01)
*H01J 49/42* (2006.01)

(52) U.S. Cl. ............ 250/310; 250/311; 250/306; 250/492.1; 250/396 R (58) Field of Classification Search .......... 250/306, 250/310, 492.1, 492.2, 396 ML, 396 R, 399
See application file for complete search history.

(56) References Cited

U.S. PATENT DOCUMENTS

| | | | |
|---|---|---|---|
| 6,566,667 B1 * | 5/2003 | Partlo et al. ........ | 250/504 R |
| 6,781,296 B2 | 8/2004 | Mensinger | |
| 6,949,752 B2 | 9/2005 | Okura et al. | |
| 7,042,145 B2 | 5/2006 | Movchan et al. | |
| 7,064,477 B2 * | 6/2006 | Magera et al. ........ | 313/336 |
| 2005/0001178 A1 * | 1/2005 | Parker et al. ........ | 250/494.1 |

* cited by examiner

*Primary Examiner*—Jack I Berman
*Assistant Examiner*—Brooke Purinton
(74) *Attorney, Agent, or Firm*—Okamoto & Benedicto LLP (57) ABSTRACT

One embodiment relates to an electron beam apparatus for inspecting or reviewing a manufactured substrate. The apparatus includes a cathode, an extraction electrode, a lens electrode, an anode, deflectors, electron lenses, and a detector. The extraction voltage is positive relative to the cathode voltage, such that electrons are emitted from the cathode. Advantageously, the lens voltage is positive relative to the extraction voltage, such that electrons are accelerated from the extraction electrode to the lens electrode while the electrons are condensed to form an electron beam. The electron beam is transmitted through an opening of the anode and is controllably deflected to scan it over an area of the surface. The detector detects secondary electrons from the substrate so as to form an image of the scanned area. Other embodiments and features are also disclosed.

10 Claims, 6 Drawing Sheets

(Accelerating Electrostatic Lens Gun)

FIG. 1

FIG. 2
(Decelerating Electrostatic Lens Gun)

FIG. 3
(Decelerating Electrostatic Lens Method)

FIG. 4
(Accelerating Electrostatic Lens Gun)

FIG. 5
(Accelerating Electrostatic Lens Method)

FIG. 6
(Accelerating Electrostatic Lens Gun)

ACCELERATING ELECTROSTATIC LENS GUN FOR HIGH-SPEED ELECTRON BEAM INSPECTION

BACKGROUND OF THE INVENTION

1. Field of the Invention

The present invention relates to semiconductor manufacturing. More particularly, the present invention relates to electrical beam inspection for semiconductor manufacturing.

2. Description of the Background Art

Automated inspection and review systems are important in process control and yield management for the semiconductor and related microelectronics industries. Such systems include optical and electron beam (e-beam) based systems.

Despite recent advances in electron beam inspection and review, further improvement may be made. For example, it is typically desirable to increase the resolution of an inspection or review system. Resolution may be defined as the smallest distance apart that two point may be distinguishable as separate points. Current e-beam inspection and review systems have resolutions of typically about 100 nanometers (0.1 micrometers). Generally, the higher the resolution, the smaller the defects that may be detected and characterized by the automated inspection and review systems. In other words, the resolution of an e-beam system limits the smallness of the features that may be detected and characterized. Hence, in order to detect and characterize smaller and smaller features on semiconductors and other specimens, it is desirable to increase the achievable resolution of the system.

E-beam inspection and review systems typically operate by scanning an incident (primary) electron beam over an area of a specimen being examined. One factor influencing resolution of such an e-beam inspection or review system is the spot size of the incident electron beam. Generally speaking, the smaller the spot size, the higher the achievable resolution. Hence, it is desirable to reduce the spot size of the incident electron beam.

Unfortunately, reducing the spot size often leads to the disadvantage of a lower beam current. A lower beam current is undesirable as it increases the time needed to image a specimen being inspected or reviewed. This results in a lower throughput for the system.

What is needed is a way to decrease the spot size of the incident electron beam in an e-beam inspection or review system without a corresponding decrease in the beam current. In other words, it is desirable to generate a primary electron beam with both a small spot size and a high beam current for use in an e-beam inspection or review system.

SUMMARY

One embodiment relates to an electron beam apparatus for inspecting or reviewing a manufactured substrate. The apparatus includes a cathode, an extraction electrode, a lens electrode, an anode, deflectors, electron lenses, and a detector. The extraction voltage is positive relative to the cathode voltage, such that electrons are emitted from the cathode. Advantageously, the lens voltage is positive relative to the extraction voltage, such that electrons are accelerated from the extraction electrode to the lens electrode while the electrons are condensed to form an electron beam. The electron beam is transmitted through an opening of the anode and is controllably deflected to scan it over an area of the surface. The detector detects secondary electrons from the substrate so as to form an image of the scanned area.

Other embodiments and features are also described herein.

DETAILED DESCRIPTION

Electron guns are used to generate incident electron beams of low landing energy for use in an e-beam inspection or review apparatus. Electron guns include magnetic lens guns and electrostatic lens guns.

Magnetic lens guns use magnetic lens(es) to focus or condense the electron beam. Advantageously, the magnetic lens provides low lens aberrations. However, they are difficult to make compatible with the high vacuum, high bake temperature and tight mechanical tolerance requirements of thermal field emission (TFE) cathodes. TFE cathodes advantageously provide for high beam currents.

Electrostatic lens guns use electrostatic lens(es) to focus or condense the electron beam. Unfortunately, conventional electrostatic lens guns for use in e-beam inspection or review apparatus generally have worse lens aberrations than magnetic lens guns. The higher lens aberrations results in beam spot sizes that are typically 10 to 20 percent larger than beam spot sizes for a comparable magnetic lens gun (under conditions where other parameters, such as beam current, are the same).

The present application discloses an inspection or review apparatus which uses an accelerating electrostatic lens gun. The accelerating electrostatic lens gun advantageously achieves smaller beam spot sizes similar to a magnetic lens gun, while being more compatible with the high vacuum, high bake temperature and tight mechanical tolerance requirements of TFE cathodes.

By using a TFE cathode and an accelerating electrostatic lens, the incident electron beam in the inspection or review apparatus may be generated in such a way as to have both a small spot size and a high beam current. This is particularly advantageous in inspection or review applications where both high resolution and high throughput are very desirable.

Figure 1:
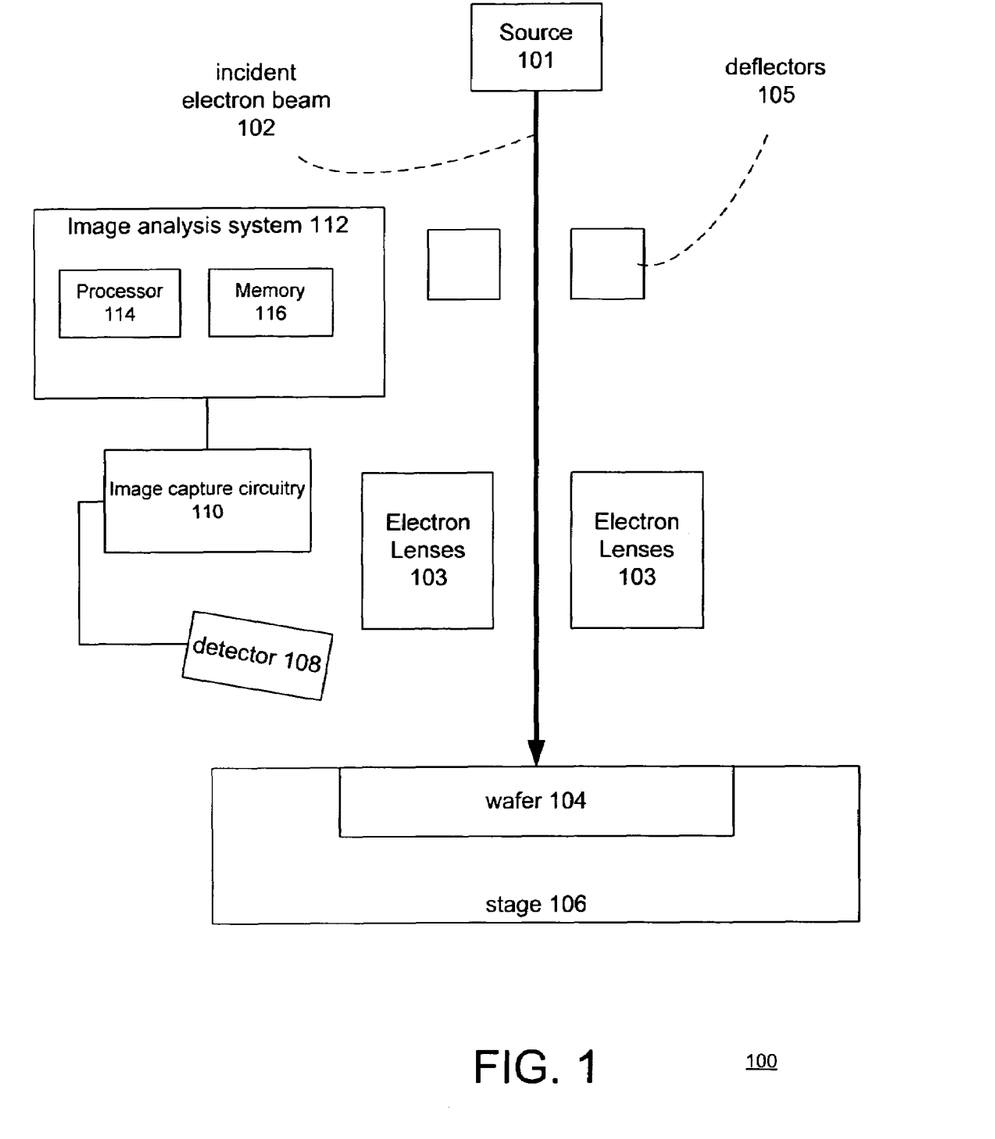
FIG. 1 is a schematic diagram depicting an electron beam inspection or review apparatus in accordance with an embodiment of the invention.

FIG. 1 is a schematic diagram depicting an electron beam inspection or review apparatus 100 in accordance with an embodiment of the invention. The electron beam apparatus 100 comprises, among other components, an electron gun or source 101, condenser lenses (not depicted), beam deflectors 105, electron lenses 103, a detection system 108, image capture circuitry 110, and an image analysis system 112.

The electron gun or source 101 generates an incident electron beam 102. In accordance with an embodiment of the invention, the electron gun or source 101 comprises an electrostatic lens gun, such as described further below in relation to FIGS. 2 through 6.

One or more electron lens 103 focuses the beam 102 so that it impinges upon a surface of a semiconductor wafer (or other substrate) 104. The wafer 104 is shown as being held in a stage 106. Deflectors 105 may be used to scan the beam 102 over the area being imaged.

A stage voltage is applied to the stage 106. The difference between the stage voltage and the voltage of the cathode source determines the landing energy of the electrons as they impinge upon the substrate surface. A typical landing energy is one thousand (1,000) electron-volts for an inspection or review apparatus. Of course, the landing energy may be varied over a range by making appropriate adjustments to the parameters of the apparatus.

A detector 108 for detecting secondary or scattered electrons is also depicted. For example, the stage 106 may be electrically grounded, and a positive voltage may be applied to the detector 108 so as to attract the scattered electrons. Image capture circuitry 110 may be configured with buffers to capture image frames from the detector 108. The image capture circuitry 110 may also be configured to process the image frames, for example, by accumulating or averaging frames.

An image analysis system 112 may be configured to retrieve, further process, and analyze the image data. The image analysis system 112 may comprise, for example, one or more processor 114 and memory 116 which is communicatively coupled to the processor 114 (for example, by way of a bus communication system). The image analysis system 112 may also include a display (not shown), such as a monitor screen, and a user input (also not shown), such as a keyboard and mouse.

The memory 116 may be configured with processor-executable code so as to perform steps to detect, localize, and/or classify defects of interest based on image processing algorithms for the purpose of inspection or review of semiconductor substrates. The inspection may be performed during the semiconductor manufacturing process, where high throughputs are desirable.

Figure 2:
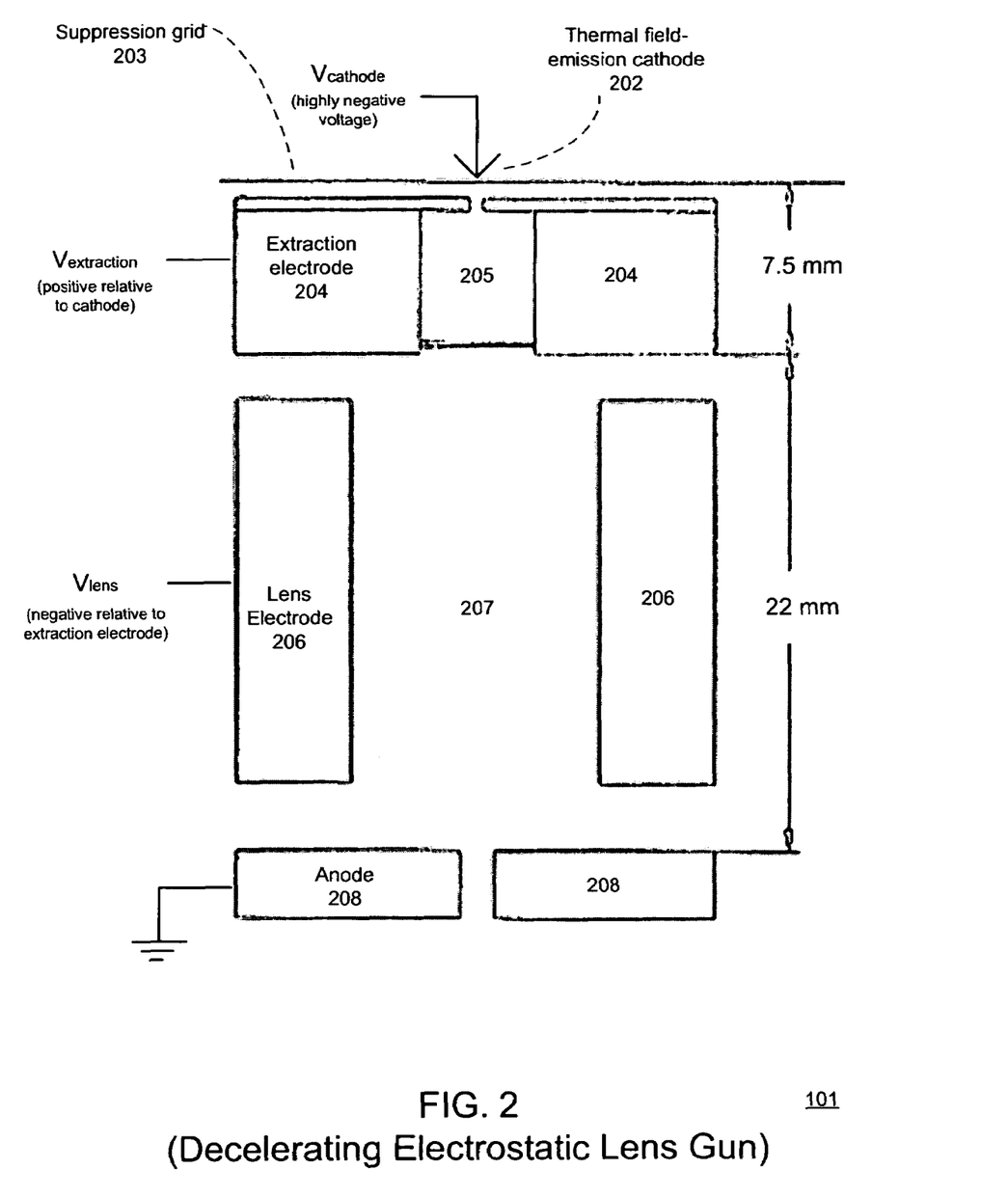
FIG. 2 is a cross-sectional schematic diagram of an electron beam gun with a decelerating electrostatic lens for an electron beam inspection or review apparatus.

FIG. 2 is a cross-sectional schematic diagram of an electron beam gun 101 with a decelerating electrostatic lens for an electron beam inspection or review apparatus 100. In this case, the gun 101 includes a cathode 202, an extraction electrode 204, a lens electrode 206, and an anode 208. Of course, while the figure shows the components in cross-section, the actual components are three-dimensional. For example, the extraction electrode 204, lens electrode 206, and anode 208 may be cylindrical in three dimensions.

In the specific implementation shown, the distance from the bottom of the extraction electrode 204 to the tip of the cathode 202 is 7.5 millimeters (mm), and the distance from the bottom of the extraction electrode 204 to the top of the anode 208 is 22 mm. Gaps are shown between the various components. These gaps may comprise insulating material.

The voltages applied to the various electrodes are labeled in the diagram. Note that it is the differences in voltage which affect the movement of the electrons. Hence, the absolute values of the applied voltages may vary depending on the specific implementation.

The cathode 202 may be embodied in a thermal field emission (TFE) cathode, which may also be called a hot-field-emission cathode. The TFE cathode may comprise, for example, a heated tungsten Schottky emitter etched to a tip and coated with Zirconium Oxide (ZrO). TFE cathodes advantageously provide high beam currents.

In the implementation shown, a high negative voltage, $V_{cathode}$, is applied to the cathode 202. The extraction electrode 204 has applied to it a voltage, $V_{extraction}$, which is positive relative to $V_{cathode}$. The difference in voltage between $V_{cathode}$ and $V_{extraction}$ causes a strong electrostatic field between them. The electrostatic field causes emission of electrons from the cathode 202 to the open space region 205 of the extraction electrode 204. The suppression grid 203 is configured with an applied voltage and positioned so as to control stray electrons.

In this case, the lens electrode 206 is configured to be a decelerating electrostatic lens. As such, the voltage, $V_{lens}$, which is applied to the lens electrode 206 is negative relative to $V_{extraction}$. The negative voltage difference decelerates the electrons as they pass through the open space region 207 of the decelerating lens electrode 206. The deceleration of the electrons and the specific configuration (shape and placement) of the lens electrode 206 result in a focusing or condensing effect on the electron beam.

Per the implementation shown, the anode 208 is held at electrical ground (i.e. at zero voltage). Electrical ground is positive relative to $V_{lens}$ (the voltage applied to the decelerating lens electrode 206). The positive voltage difference accelerates the electron beam as it travels to the anode 208. The generated electron beam is emitted from an opening in the anode 208.

Unfortunately, the use of a decelerating electrostatic lens causes higher aberrations (away from the optical axis of the apparatus) in the electron beam 102 (relative to using a magnetic lens at comparable beam energy and beam current). Applicant believes that these higher aberrations are due, at least in part, due to the greater time spent by the electrons in the open space region 207 of the decelerating lens electrode 206. The greater time spent by the electrons causes higher electron-to-electron interactions, and hence the higher aberrations. The higher aberrations result in beam spot sizes for a decelerating electrostatic lens gun that are 10% to 20% larger than beam spot sizes for a comparable magnetic lens gun.

Figure 3:
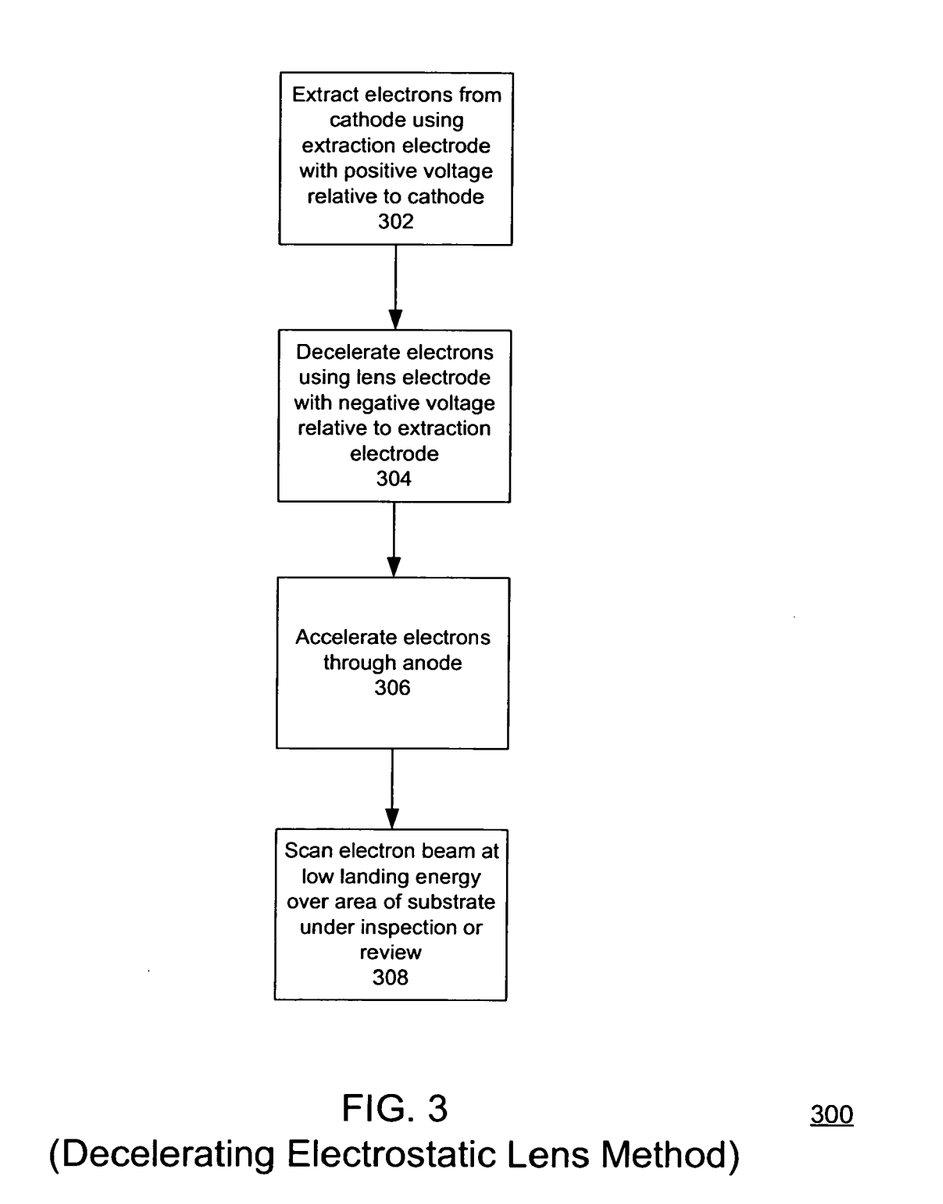
FIG. 3 is a flow chart of a method of generating an electron beam using an electron beam gun with a decelerating electrostatic lens for inspection or review of a substrate.

FIG. 3 is a flow chart of a method 300 of generating an electron beam using an electron beam gun 101 with a decelerating electrostatic lens for inspection or review of a substrate 104. An example of such a decelerating electrostatic lens gun is discussed above in relation to FIG. 2.

Per the method 300, an electrostatic field is used to extract (302) electrons from the cathode 202. This is accomplished by applying voltages such that the voltage of the extraction electrode is positive relative to the cathode voltage.

In this case, the electrons are decelerated (304) using a decelerating electrostatic lens. The decelerating electrostatic lens may comprise a lens electrode 206 which has applied thereto a voltage which is negative relative to the voltage on the extraction electrode. The negative voltage difference decelerates (304) the electrons as they pass through the open space region 207 of the decelerating lens electrode 206.

The voltage applied to the anode 208 is positive relative to the voltage applied to the decelerating lens electrode 206. The positive voltage difference accelerates (306) the electron beam as travels to the anode 208, and the accelerated electron beam passes through an opening in the anode 208.

The electron beam 102 generated by the gun 101 is focused by electron (objective) lenses 103 onto a beam spot on the wafer 104 or other substrate being inspected or reviewed for defects. The beam spot may be scanned (308) over an area of the substrate under inspection or review by controllable deflection using magnetic or electrostatic deflectors 105.

As described above, the use of a decelerating electrostatic lens causes higher aberrations (away from the optical axis) in the electron beam 102 (relative to using a magnetic lens at comparable beam energy and beam current). The higher aberrations result in beam spot sizes for a decelerating electrostatic lens gun that are 10% to 20% larger than beam spot sizes for a comparable magnetic lens gun.

Figure 4:
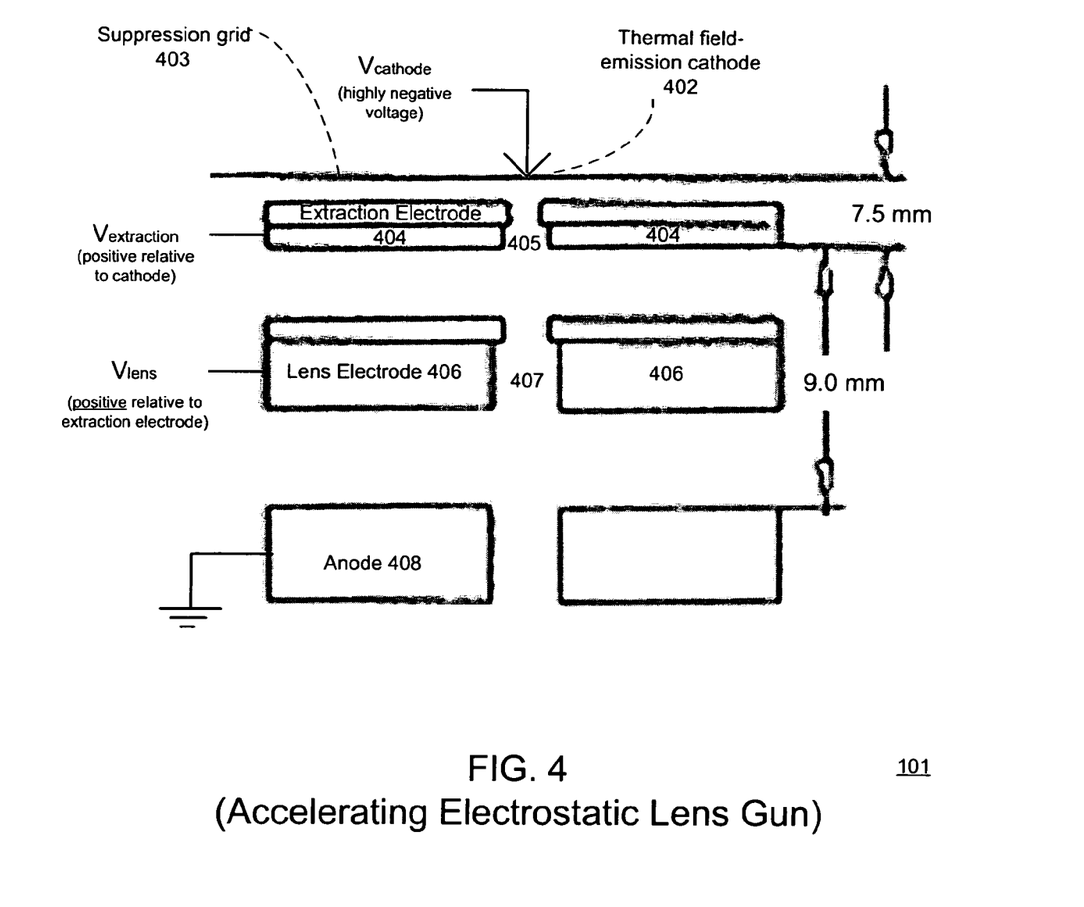
FIG. 4 is a cross-sectional schematic diagram of an electron beam gun with an accelerating electrostatic lens for an electron beam inspection or review apparatus in accordance with an embodiment of the invention.

FIG. 4 is a cross-sectional schematic diagram of an electron beam gun 101 with an accelerating electrostatic lens for an electron beam inspection or review apparatus 100 in accordance with an embodiment of the invention.

In this case, the gun 101 includes a cathode 402, an extraction electrode 404, a lens electrode 406, and an anode 408. Of course, while the figure shows the components in cross-section, the actual components are three-dimensional. For example, the extraction electrode 404, lens electrode 406, and anode 408 may be cylindrical in three dimensions.

In the specific implementation shown, the distance from the bottom of the extraction electrode 404 to the tip of the cathode 402 is 7.5 millimeters (mm), and the distance from the bottom of the extraction electrode 404 to the top of the anode 408 is 9.0 mm. The former distance (7.5 mm between 402 and 404) is the same as in the comparable implementation of the decelerating electrostatic lens gun shown in FIG. 2. Meanwhile, the latter distance (9.0 mm between 404 and 408) is substantially shorter in the implementation of the accelerating electrostatic lens gun shown in FIG. 4 than the corresponding distance (22 mm) in the comparable implementation of the decelerating electrostatic lens gun shown in FIG. 2. Gaps are shown between the various electrodes in FIG. 4. These gaps may include insulating material.

The voltages applied to the various electrodes are labeled in the diagram. Note that it is the differences in voltage which affect the movement of the electrons. Hence, the absolute values of the applied voltages may vary depending on the specific implementation.

The cathode 402 may be embodied in a thermal field emission (TFE) cathode, which may also be called a hot-field-emission cathode. The TFE cathode may comprise, for example, a heated tungsten Schottky emitter etched to a tip and coated with Zirconium Oxide (ZrO). TFE cathodes advantageously provide high beam currents.

In the implementation shown, a high negative voltage, $V_{cathode}$, is applied to the cathode 402. The extraction electrode 404 has applied to it a voltage, $V_{extraction}$, which is positive relative to $V_{cathode}$. The difference in voltage between $V_{cathode}$ and $V_{extraction}$ causes a strong electrostatic field between them. The electrostatic field causes emission of electrons from the cathode 402 to the open space region 405 of the extraction electrode 404. The suppression grid 403 has a voltage applied thereto and is configured so as to control stray electrons.

In this case, the lens electrode 406 is configured to be an accelerating electrostatic lens. As such, the voltage, $V_{lens}$, which is applied to the lens electrode 406 is positive relative to $V_{extraction}$. The positive voltage difference accelerates the electrons as they pass through the open space region 407 of the accelerating lens electrode 406. The acceleration of the electrons and the specific configuration (shape and placement) of the lens electrode 406 result in a focusing or condensing effect on the electron beam. The electron beam from the accelerating electrostatic lens electrode 406 may then be transmitted through the opening in the anode 408.

The voltage ($V_{lens}$) of the lens electrode 406 relative to the voltage of the anode 408 determines whether the electrons are accelerated or decelerated between the lens electrode 406 and the anode 408. If $V_{lens}$ is negative relative to the voltage of the anode 408, then there is an electrostatic field between the two which accelerates the electrons through the opening in the anode 408. On the other hand, if $V_{lens}$ is positive relative to the voltage of the anode 408, then there is an electrostatic field between the two which slows down the electrons as they pass through the opening in the anode 408.

In an example with simple numbers, the cathode voltage may be at negative ten thousand (−10,000) volts, $V_{extraction}$ may be negative five thousand (−5,000) volts, $V_{lens}$ may be positive fifteen thousand (+15,000) volts, and the anode 408 may be at electrical ground (as shown in FIG. 4). Since $V_{extraction}$ is 5,000 volts more positive relative to the cathode voltage, the electric field would draw the electrons from the cathode 402 to the open region 405 of the extraction electrode 404. Furthermore, since $V_{lens}$ is 20,000 volts more positive relative to $V_{extraction}$, the electrons would be rapidly accelerated by the lens electrode 406 from an energy level of 5,000 electron-volts to an energy level of 25,000 electron-volts. In this case, since the anode 408 at ground is 15,000 volts more negative relative to $V_{lens}$, the electrons would slow down as they pass through the opening in the anode 408. The electrons exit from the opening in the anode 408 with an energy level of 10,000 electron-volts. Of course, the above voltage and energy values are simplified for purposes of explanation. Actual voltage and energy values would depend upon the specific implementation, including the desired beam energy and so forth.

Advantageously, an accelerating electrostatic lens gun may be used to generate an electron beam with lower aberrations (relative to using a decelerating electrostatic lens gun at comparable beam energy and beam current). Applicant believes that the low level of aberrations (away from the optic axis of the apparatus) is due to the electrons spending less time in the open space region 407 of the lens electrode 406. By spending less time in that region, the electrons experience a lesser amount of electron-to-electron interactions. The lower aberrations result in beam spot sizes for an accelerating electrostatic lens gun (see FIG. 4) that are 10% to 20% smaller than beam spot sizes for a comparable decelerating electrostatic lens gun (see FIG. 2).

Compared to a magnetic lens gun, the achievable beam spot size for the accelerating electrostatic lens gun is similar to the beam spot size achievable by a magnetic lens gun. However, unlike the magnetic lens gun, the accelerating electrostatic lens gun is more compatible with the high vacuum, high bake temperature, and tight mechanical tolerance requirements of TFE cathodes.

Figure 5:
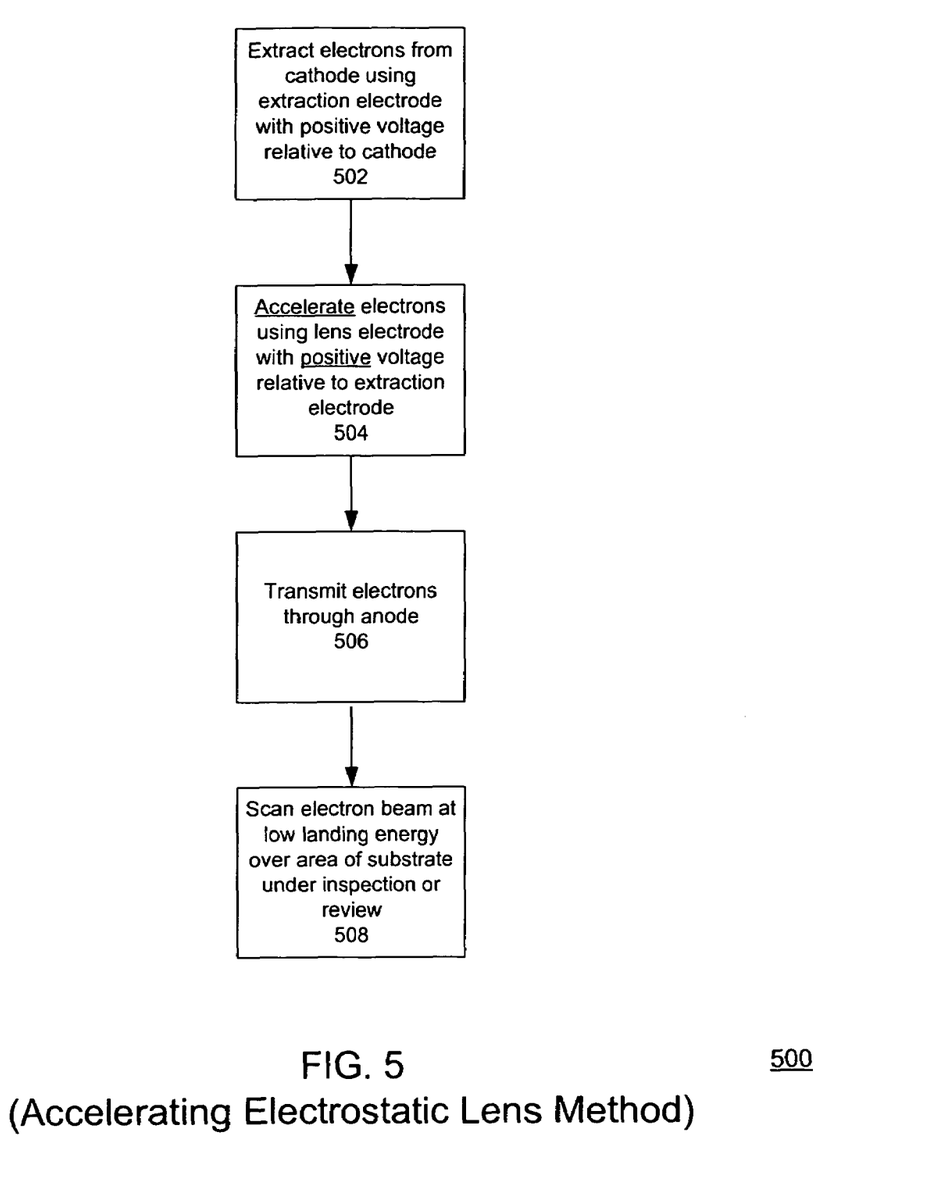
FIG. 5 is a flow chart of a method of generating an electron beam using an electron beam gun with an accelerating electrostatic lens for inspection or review of a substrate in accordance with an embodiment of the invention.

FIG. 5 is a flow chart of a method 500 of generating an electron beam using an electron beam gun 101 with an accelerating electrostatic lens for inspection or review of a substrate 104 in accordance with an embodiment of the invention. An example of such an accelerating electrostatic lens gun is discussed above in relation to FIG. 4.

Per the method 500, an electrostatic field is used to extract (502) electrons from the cathode 402. This is accomplished by applying voltages such that the voltage of the extraction electrode is positive relative to the cathode voltage. Preferably, the cathode 402 is a thermal field emitting (TFE) cathode, which may also be called a hot-field-emission cathode.

In this case, the electrons are accelerated (504) using an accelerating electrostatic lens. The accelerating electrostatic lens may comprise a lens electrode 406 which has applied thereto a voltage which is positive relative to the voltage on the extraction electrode. The positive voltage difference accelerates (504) the electrons as they pass through the open space region 407 of the accelerating lens electrode 406.

The voltage applied to the anode 408 may be positive or negative relative to the voltage applied to the accelerating lens electrode 406. A positive voltage difference accelerates the electron beam as it travels to the anode 408, and a negative voltage difference decelerates or slows down the electron beam as it travels to the anode 408. A simple example of the latter is discussed above in relation to FIG. 4. In either case, the electrons are transmitted (506) through an opening in the anode 408.

Finally, the electron beam 102 generated by the gun 101 is focused by electron (objective) lenses 103 onto a beam spot on the wafer 104 or other substrate being inspected or reviewed for defects. The beam spot may be scanned (508) over an area of the substrate under inspection or review by controllable deflection using magnetic or electrostatic deflectors 105.

In one example, a stage voltage may be applied such that the landing energy of the electrons is relatively low. The landing energy of the electrons is determined by the voltage difference between the cathode filament 402 and the voltage at the substrate. For example, if the cathode voltage is negative ten thousand (−10,000) volts, and the stage voltage is negative nine thousand (−9,000) volts, then the landing energy would be one thousand (1,000) electron volts.

As described above, an accelerating electrostatic lens gun may be used in an inspection or review apparatus to generate an electron beam with lower aberrations (relative to using a decelerating electrostatic lens gun at comparable beam energy and beam current). The lower aberrations result in beam spot sizes for an accelerating electrostatic lens gun that are 10% to 20% smaller than beam spot sizes for a comparable decelerating electrostatic lens gun.

Compared to a magnetic lens gun, the achievable beam spot size for the accelerating electrostatic lens gun is similar to the beam spot size achievable by a magnetic lens gun. However, unlike the magnetic lens gun, the accelerating electrostatic lens gun is more compatible with the high vacuum, high bake temperature, and tight mechanical tolerance requirements of TFE cathodes.

Figure 6:
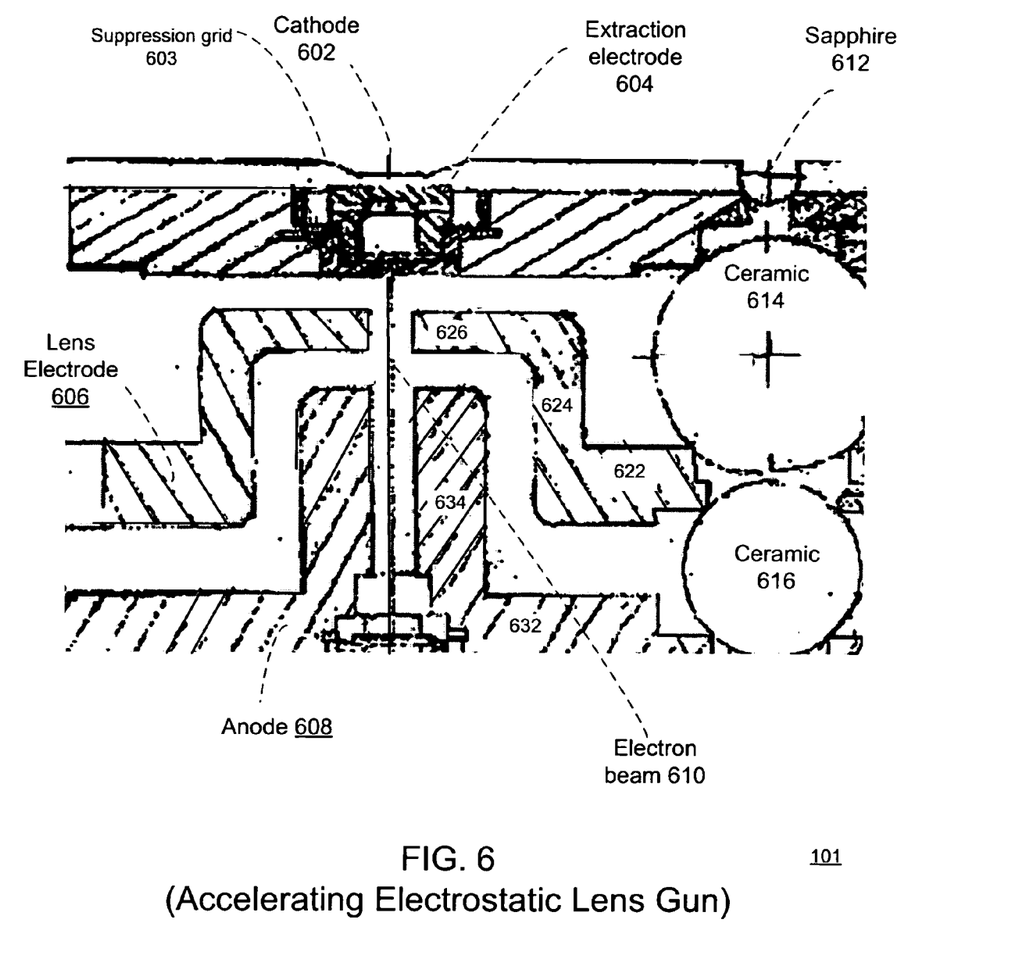
FIG. 6 is a cross-sectional engineering diagram of an electron beam gun with an accelerating electrostatic lens for an electron beam inspection or review apparatus in accordance with an embodiment of the invention.

FIG. 6 is a cross-sectional engineering diagram of an electron beam gun 101 with an accelerating electrostatic lens for an electron beam inspection or review apparatus in accordance with an embodiment of the invention.

In this case, the gun 101 includes a cathode 602, an extraction electrode 604, a lens electrode 606, and an anode 608. Of course, while the figure shows the components in cross-section, the actual components are three-dimensional.

The cathode 602 may be embodied in a thermal field emission (TFE) cathode, which may also be called a hot-field-emission cathode. The TFE cathode may comprise, for example, a heated tungsten Schottky emitter etched to a tip and coated with Zirconium Oxide (ZrO). TFE cathodes advantageously provide high beam currents.

In the implementation shown, a high negative voltage (the cathode voltage) is applied to the cathode 602. The extraction electrode 604 has applied to it an extraction voltage which is positive relative to the cathode voltage. In addition, a sapphire insulating component 612 is preferably used to structurally and electrically separate the cathode 602 from the extraction electrode 604. In alternate embodiment, different insulating materials may be used.

The difference between the cathode and extraction voltages causes a strong electrostatic field between them. The electrostatic field causes emission of electrons from the cathode 602 to the open space region 605 of the extraction electrode 604. The suppression grid 603 has a voltage applied thereto and is configured so as to control stray electrons.

In the specific implementation shown, the lens electrode 606 comprises a base section 622, a connecting section 624, and a focusing-field generation section 626. A ceramic insulating component 614 may preferably be used to separate the base section 622 of the lens electrode 606 from the extraction electrode 604. The connecting section 624 connects the base section 622 to the focusing-field section 626. The focusing-field generation section 626 is the section closest to the electron beam 610, and the electrostatic potential from the focusing-field generation section 626 provides the focusing effect. Advantageously, the configuration shown for the lens electrode 606 suppresses electrical arcing between the extraction and lens electrodes.

In accordance with an embodiment of the invention, the lens electrode 606 is configured to be an accelerating electrostatic lens. As such, the voltage which is applied to the focusing-field generation section 626 (the lens voltage) is positive relative to the extraction voltage. The positive voltage difference accelerates the electrons as they pass through the opening of the focusing-field generation section 626. The accelerating field and the specific configuration (shape and placement) of the focusing-field generation section 626 result in a focusing or condensing effect on the electron beam. The electron beam 610 may then be transmitted through the opening in the anode 608.

In the specific implementation shown, the anode 608 comprises a base section 632 and a field generation section 634. The field generation section 634 is the section closest to the electron beam 610. As shown, the field generation section 634 may comprise an elongated section with an opening through which the electron beam 610 is transmitted, such that the electron beam travels along the elongated dimension. The elongated section 634 of the anode 608 may be configured parallel to the connecting section 624 of the lens electrode 606, and the base section 632 of the anode 608 may be configured parallel to the base section 622 of the lens electrode 606. In addition, a ceramic insulating component 616 may preferably be used to structurally and electrically separate the base section 632 of the anode 608 from the base section 622 of the lens electrode 606. Advantageously, the configuration shown for the anode 608 relative to the lens electrode 606 suppresses electrical arcing between the anode and the lens electrode.

The lens voltage relative to the anode voltage determines whether the electrons are accelerated or decelerated as the beam 610 between the lens electrode 606 and the anode 608. If the lens voltage is negative relative to the anode voltage, then there is an electrostatic field between the two which accelerates the electrons through the opening in the anode 608. On the other hand, if the lens voltage is positive relative to the anode voltage, then there is an electrostatic field between the two which slows down the electrons as they pass through the opening in the anode 608.

Advantageously, an accelerating electrostatic lens gun may be used to generate an electron beam with lower aberrations (relative to using a decelerating electrostatic lens gun at comparable beam energy and beam current). The lower aberrations result in beam spot sizes for an accelerating electrostatic lens gun that are 10% to 20% smaller than beam spot sizes for a comparable decelerating electrostatic lens gun.

Compared to a magnetic lens gun, the achievable beam spot size for the accelerating electrostatic lens gun is similar to the beam spot size achievable by a magnetic lens gun. However, unlike the magnetic lens gun, the accelerating electrostatic lens gun is more compatible with the high vacuum, high bake temperature, and tight mechanical tolerance requirements of TFE cathodes.

The above-described diagrams are not necessarily to scale and are intended be illustrative and not limiting to a particular implementation.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. An electron beam apparatus for inspecting or reviewing a manufactured substrate, the apparatus comprising:
    a cathode at a cathode voltage;
    an extraction electrode at an extraction voltage, wherein the extraction voltage is positive relative to the cathode voltage, such that electrons are emitted from the cathode;
    a lens electrode at a lens voltage, wherein the lens voltage is positive relative to the extraction voltage, such that electrons are accelerated from the extraction electrode to the lens electrode while the electrons are condensed to form an electron beam, further wherein the lens electrode includes a base section, a focusing-field generation section, and a connecting section which connects the base section and the focusing-field generation section; and
    an anode with an opening through which the electron beam is transmitted, wherein the anode includes a base section and a field generation section, further wherein the field generation section of the anode is configured with an elongated dimension which lies parallel to the connecting section of the lens electrode;
    deflectors configured to controllably deflect the electron beam to scan the electron beam over an area of the substrate;
    electron lenses configured to focus the electron beam onto a spot on a surface of the substrate; and
    a detector configured to detect secondary electrons from the substrate so as to form an image of the scanned area.

2. The apparatus of claim 1, wherein the cathode comprises a thermal field emitter.

3. The apparatus of claim 2, further comprising a suppression grid configured between the cathode and the extraction electrode.

4. The apparatus of claim 1, further comprising a first insulating component which structurally and electrically separates the base section of the lens electrode from the extraction electrode.

5. The apparatus of claim 4, wherein the first insulating component comprises a ceramic material.

6. The apparatus of claim 4, further comprising a second insulating component which structurally and electrically separates the base section of the lens electrode from the base section of the anode.

7. The apparatus of claim 6, wherein the second insulating component comprises a ceramic material.

8. The apparatus of claim 7, further comprising a third insulating component which structurally and electrically separates the extraction electrode from the cathode.

9. The apparatus of claim 8, wherein the third insulating component comprises sapphire.

10. A method for inspecting or reviewing a manufactured substrate using an electron beam apparatus, the method comprising:
    applying a cathode voltage to a cathode;
    applying an extraction voltage to an extraction electrode, wherein the extraction voltage is positive relative to the cathode voltage, such that electrons are emitted from the cathode;
    applying a lens voltage to a lens electrode, wherein the lens voltage is positive relative to the extraction voltage, such that electrons are accelerated from the extraction electrode to the lens electrode while the electrons are condensed to form an electron beam, further wherein the lens electrode includes a base section, a focusing-field generation section, and a connecting section which connects the base section and the focusing-field generation section;
    transmitting the electron beam through an opening in an anode, wherein the anode includes a base section and a field generation section, further wherein the field generation section of the anode is configured with an elongated dimension which lies parallel to the connecting section of the lens electrode;
    controllably deflecting the electron beam to scan the electron beam over an area of the substrate;
    focusing the electron beam onto a spot on a surface of the substrate; and
    detecting secondary electrons from the substrate so as to form an image of the scanned area.

* * * * *